United States Patent

Hunziker et al.

[11] Patent Number: 4,511,370
[45] Date of Patent: Apr. 16, 1985

[54] PROCESS FOR THE UTILIZATION OF HOUSEHOLD RUBBISH OR GARBAGE AND OTHER ORGANIC WASTE PRODUCTS FOR THE PRODUCTION OF METHANE GAS

[76] Inventors: Martin Hunziker, Speerstrasse 50, Zürich; Albert Schildknecht, Dorfstrasse 45, Oetwil a.d.Limmat, both of Switzerland

[21] Appl. No.: 406,246
[22] PCT Filed: Dec. 4, 1981
[86] PCT No.: PCT/CH81/00137
§ 371 Date: Aug. 4, 1982
§ 102(e) Date: Aug. 4, 1982
[87] PCT Pub. No.: WO82/02059
PCT Pub. Date: Jun. 24, 1982

[30] Foreign Application Priority Data
Dec. 12, 1980 [CH] Switzerland ............... 9215/80

[51] Int. Cl.³ ............ C02F 11/04; C02F 3/30; C12P 5/02
[52] U.S. Cl. .................. 48/197 A; 48/209; 210/603; 210/612; 210/613; 210/630; 435/801
[58] Field of Search ............. 48/209, 197 A, 111; 210/603, 612, 613, 622, 630, 180; 435/167, 801

[56] References Cited
U.S. PATENT DOCUMENTS

| | | | |
|---|---|---|---|
| 3,838,199 | 9/1974 | Coe et al. | 210/603 |
| 4,022,665 | 5/1977 | Ghosh et al. | 435/801 |
| 4,057,401 | 11/1977 | Boblitz | 48/111 |
| 4,213,857 | 7/1980 | Ishida et al. | 210/612 |
| 4,246,099 | 1/1981 | Gould et al. | 210/603 |
| 4,274,838 | 6/1981 | Dale et al. | 48/197 A |

FOREIGN PATENT DOCUMENTS 2464297  3/1981  France .
2466502  4/1981  France .

Primary Examiner—S. Leon Bashore
Assistant Examiner—Karen M. Hastings
Attorney, Agent, or Firm—Weingarten, Schurgin, Gagnebin & Hayes

[57] ABSTRACT

Non-organic substances are separated from household garbage and the organic substances are fed in proportioned manner into a mixing tank (5) and converted into slurry by adding liquid. The slurry is crushed for homogenization purposes in a crushing means (10, 11) and passed into a closed holding container (13). It is then fed over a heat exchanger (15) and heated to 55° to 60° C. The slurry passes into a plurality of reaction vessels (16) in which the methane gas and carbon dioxide are produced. In a separating plant (22), the mixture of gaseous products is broken down into its components and some of the methane gas is recycled by bubbling it through both the holding tank and the reaction tank, the remainder being stored in gasholders (23). The organic substances are degraded much more rapidly through increasing the degradation temperature and as a result constructional expenditure can be reduced.

11 Claims, 2 Drawing Figures

PROCESS FOR THE UTILIZATION OF HOUSEHOLD RUBBISH OR GARBAGE AND OTHER ORGANIC WASTE PRODUCTS FOR THE PRODUCTION OF METHANE GAS

The invention relates to a process for the utilization of household rubbish or garbage and other waste products containing organic substances by the decomposition of these substances in reaction chambers, accompanied by the production of methane gas. The substances are conducted in anaerobic and aerobic phases. The invention also relates to a plant for performing this process.

In known processes, the waste products produced by humans and animals are eliminated, particularly by refuse incineration and composting. In addition, sewage treatment plants are used for treating the contaminated water and feces, the sludge resulting from these processes being dried and either used as fertiliser or burnt. It is also known to decompose the sludge obtained in sewage treatment plants by methane-producing bacteria, the resulting methane gas being used for producing energy and heat. Although the hitherto known processes are relatively effective, they suffer from the disadvantage that the time required for the bacterial degradation of the organic substances is too long. This leads to the erection of treatment installations which are large compared with the waste product quantities to be processed.

The goal of the invention is to so develop a process for producing methane gas of the aforementioned type, that the bacterial degradation of the organic waste can be considerably accelerated, without the degradation process being performed any the less effectively.

According to the invention, this goal is achieved in that in the anaerobic phase, heat is supplied to the substances brought into the liquid state prior to their entry into the reaction chambers.

The process according to the invention is carried out in a plant in which the part of the plant used for the anaerobic phase comprises a holding container, at least one reaction vessel, and a heating device which is positioned between the waiting holding container and the reaction vessel for heating the substances.

The invention is described in greater detail hereinafter relative to an embodiment and the attached drawings, wherein.

The invention is based on the consideration that the bacterial degradation of organic waste can be accelerated if thermophilic bacteria can be used. This is achieved if the degradation temperature can be kept at 50° to 60° C. Although this requires a supply of heat for heating the organic substances, it reduces the residence time of the degradable substances in the reaction vessels provided for them by approximately ⅔ compared with the hitherto known processes, so that constructional expenditure is significantly reduced and as a result the economic operation of such a plant is greatly improved.

Figure 1:
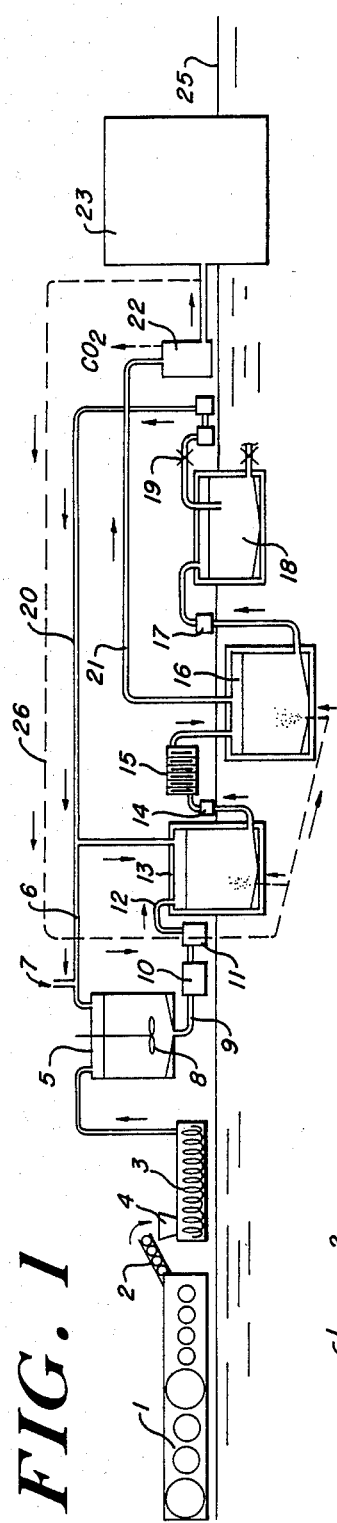
FIG. 1 shows a diagrammatic view of a plant according to the invention in elevation.
Figure 2:
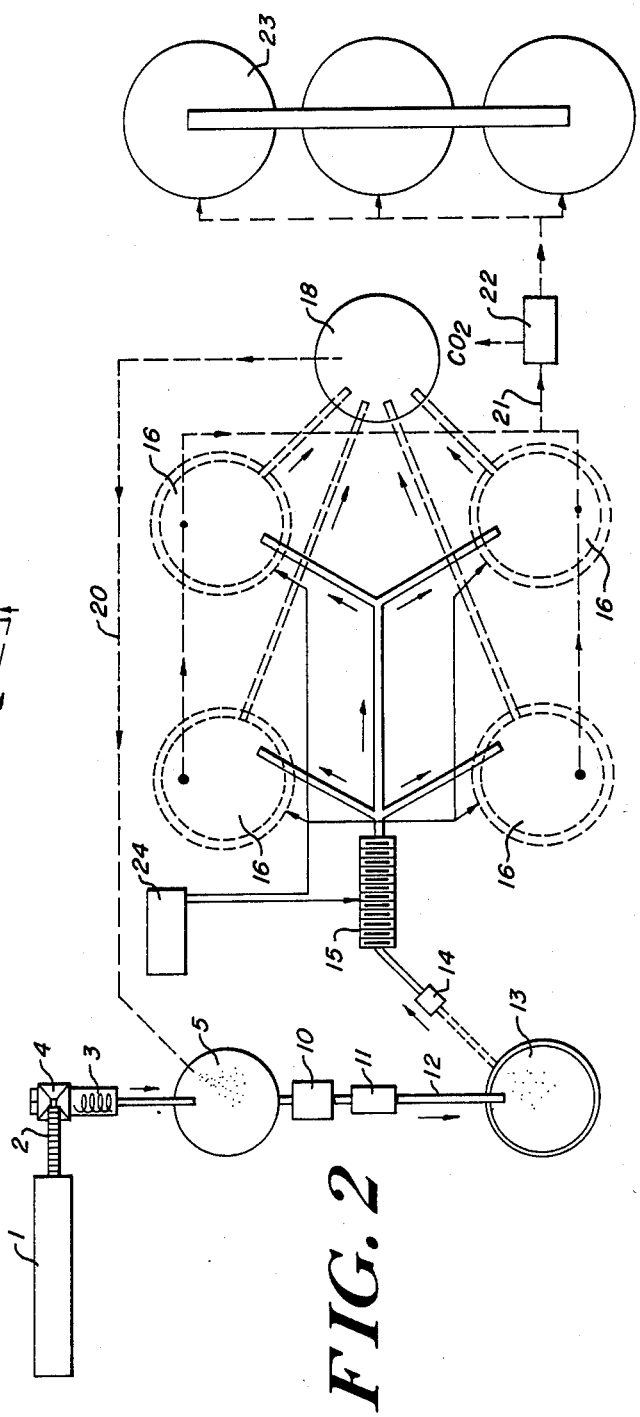
FIG. 2 shows a plan view of the plant according to FIG. 1.

The plant shown in FIGS. 1 and 2 is used for the processing of household refuse and garbage and the organic substances separated therefrom can be mixed with other organic waste materials, e.g. manure, liquid manure, sewage sludge, etc.

The household refuse introduced into the plant is firstly supplied to a diagrammatically represented sorting plant 1 in which the organic substances are separated from the remaining materials such as e.g. metals, glass, plastics, cardboard, etc. The organic substances are fed through a conveyor 2 to a proportioning means 3 e.g. a proportioning screw, which has a slightly conically constructed charging hopper 4 on its top surface. The organic substances are fed to a mixing tank 5 from the outlet side of the proportioning screw 3. Liquid is fed into the mixing tank 5 via a liquid supply pipe 6. Supply pipe 6 has a connection 7 through which additional organic materials can be introduced into mixing tank 5, e.g. liquid manure or sewage sludge. The content of mixing tank 5 is mixed by means of a diagrammatically shown mechanical stirrer 8. Mixing tank 5 has no special means for removing oxygen and aerobic conditions prevail therein.

At the bottom of the mixing tank 5, which appropriately slopes towards the centre, a pipe 9 leads to a crushing means, which comprises a coarse crusher 10 and a following fine crusher 11. Crushers 10 and 11 are appropriately mills, e.g. disk mills and for the purpose of homogenizing the slurry formed, the fine mill crushes the material to a particle size of about 1.5 mm. The crushed organic substances are transferred by a connecting line 12 into a holding container 13, which is sealed in airtight manner. The slurry located therein is stirred by methane gas forced in under pressure through openings in the bottom of container 13. An oxygen-free mixture of slurry and methane gas is formed, which is delivered by a pump 14 through a heat exchanger into a reaction vessel 16. As anaerobic conditions prevail in waiting container 13, the decomposition of the organic substances by anaerobic bacteria start therein, so that the slurry temperature rises to about 30° C. After traversing the heat exchanger 15, e.g. a tubular exchanger, the slurry reaches a temperature of about 60° C. At this temperature, there is propagation of the thermophilic bacteria and the organic substances are degraded with a greater intensity. This leads to a mixture of carbon dioxide and methane gas, approximately in the ratio of 35% by volume carbon dioxide to 65% by volume methane gas. An intense stirring of the slurry is also maintained in reaction vessel 16 and as in the case of holding container 13 this is brought about by forcing in methane gas.

The organic substances are decomposed to approximately 80% in reaction vessel 16 and the residual slurry therein is delivered by a pump 17 to a residual sludge tank 18. In the latter, the liquid is separated from the remaining substances and conveyed by a pump 19 via a feed line 20 to mixing tank 5 and/or holding container 13, as required, in order to achieve the desired composition of the homogenized slurry. The sludge has a dry substance content of approximately 60%, but this proportion can be increased as a function of the conditions. It is important that the temperature is maintained at about 60° C. in the reaction vessel 16. For this purpose, vessel 16 contains heating coils subject to the action of a heat carrier.

The gas obtained in reaction vessel 16 is conveyed by a line 21 into a separating plant 22, where it is broken down into its two components carbon dioxide and methane gas, the latter then being stored in gas-holders 23. The methane gas is partly used for the stirring movement of the slurry in holding container 13 and in reaction vessel 16. The remaining methane gas can be used for operating a gas engine (not shown), which drives an electric generator. This supplies the electric power for driving electric motors, which are incorporated e.g. into the proportioning means 3, stirrer 8, mills 10, 11, pumps 14, 17, 19, conveyor 2 and proportioning screw 3. If the described plant is suitably designed, methane gas is still available, which can be used e.g. for heat production, for which purpose it is also possible to use the waste heat from the aforementioned gas engine. Thus, the plant can be operated in a self-sufficient manner, in spite of the fact that the degradation rate is considerably accelerated through the use of thermophilic bacteria and consequently through increasing the degradation temperature.

Thus, the described process takes place both in the aerobic and anaerobic phases. The aerobic phase is subdivided into an aerobic pre-phase with sorting plant 1, conveyor 2, proportioning screw 3, mixing tank 5, crushers 10 and 11, and an aerobic post-phase with the residual sludge tank 18, pump 19 and line 20. The anaerobic phase comprises holding container 13 with a temperature stage of 30° C., heat exchanger 15, reaction vessel 16 and pump 17.

FIG. 2 shows somewhat more clearly the connections within the plant. The path of the slurry is shown by the continuous and broken double lines. The transfer of the methane gas and carbon dioxide from reaction vessel 16 is indicated by a broken line. Line 20 is used for the return of the water from the residual sludge in residual sludge tank 18. The heat supply from a heat generating plant 24 to heat exchanger 15 and in the individual reaction vessel 16 is represented by the continuous single lines. FIG. 2 also shows the number of the individual plant parts required for the presently described plant, while FIG. 1 shows the position of these parts relative to the ground. Sorting plant 1, proportioning screw 3, mixing vessel 5 and crushers 10, 11 are located above the ground 25 and are also housed in a not shown building. Mixing vessel 5 is partly embedded in the ground 25, while the reaction vessel or vessels 16 are entirely located in the ground 25 and also have an effective insulation. Residual sludge tank 18 is partly in the ground 25, while pump 19, separating plant 22 and at least partly gasholder 23 are located above the ground 25.

An example of such a plant is illustrated by means of FIGS. 1 and 2. In the case of a plant which processes 27 t of fresh, unsorted domestic garbage every day, corresponding to 15 t of degradable substances, it is necessary to having a mixing vessel 5 of approximately 400 to 500 $m^3$, i.e. approximately 30 $m^3/t$. Appropriately, the mixing vessel 5 is cylindrical in order to achieve a good stirring action with stirrer 8. The waste products remain for about 24 hours in mixing vessel 5.

Following crushers 10, 11, the crushed substances, to which liquid is added from the residual sludge tank 18 until a mixture with 5 to 6% by weight dry substance is achieved, are transferred into the holding container, which also has a capacity of about 400 to 500 $m^3$. Holding container 13 is completely closed and the sludge is kept in constant movement by introduced methane gas removed following the separation plant 22 and fed in by means of line 26, cf FIG. 1. holding container 13 is also appropriately cylindrical with a conically sloping bottom and the slurry spends about 24 hours therein.

A temperature of 55° to 60° is required for the actual methane production process, of FIG. 2, which requires four reaction vessels 16 with a capacity of 500 to 600 $m^3$ in order to process the quantity of 15 t of degradable substances. The slurry is left in reaction vessel 16 for about 8 days. It is necessary during this time to drain off a certain amount of sludge every day and feed in new slurry in order to maintain a constant activity without exhaustion or saturation. Reaction vessels 16 are closed containers, which can also have a cylindrical shape with a conical bottom.

The resulting gas contains about 65% methane ($CH_4$) and 35% carbon dioxide ($CO_2$). Approximately 140 $Nm^3$ of methane gas can be produced for every ton of sorted household garbage, giving 2175 $Nm^3$ for the daily quantity of 15 t. The gas obtained has a high calorific value of approximately 40600 $kJ/Nm^3$, corresponding to 9700 Kcal and can therefore certainly be used. It is also relatively pure on leaving gasholder 23.

The residual sludge in residual sludge tank 18 still contains about 20% of substances, which in the case of 15 t daily represents about 3 t of compost with a liquid content of approximately 53%.

Obviously, the plant parts need not always be arranged exactly as in FIG. 2, e.g. the reaction vessels 16 need only partly be buried in the ground 25.

Tank 18 can also be used for pasteurizing the residual sludge or for the additional production of methane gas from the residual sludge obtained in tank 18. In the latter case, the post-phase is conducted anaerobically.

We claim:
1. A process for producing methane gas comprising the following sequential steps:
agitating a slurry of crushed organic matter and water in a substantially air tight holding tank, by bubbling methane gas through the slurry, until anaerobic bacterial action commences, as indicated by a rise in temperature of the slurry to about 30° C.;
removing the slurry from the holding tank;
heating the slurry to about 55°–60° C.;
transferring the slurry to at least one substantially air tight reaction tank;
fermenting the slurry in said reaction under anaerobic conditions at a temperature of about 55°–60° C. and agitating it by bubbling methane gas through it, to promote production of methane gas;
separating the gaseous, liquid, and solid phases from each other; and
collecting the methane gas produced.

2. Process according to claim 1, wherein the slurry has a solids content of 5–10%.

3. A process according to claim 1, further comprising:
separating the product gases to yield by-products plus methane; and
recycling part of said methane to the holding tank and the reaction tank to agitate the slurry.

4. A process according to claim 1, wherein the step of separating the liquid and solid phases is conducted in a sludge tank following the reaction tank.

5. A process according to claim 4, further comprising:
heating the contents of the sludge tank under anaerobic conditions to produce a further yield of methane.

6. A process according to claim 4, further comprising:
heating the contents of the sludge tank to a temperature sufficient to sterilize the sludge.

7. A process for producing methane gas comprising the following sequential steps:
- mixing organic matter with water to form a slurry;
- passing the slurry through a course crusher followed by a fine crusher to homogenize the slurry;
- transferring the slurry to a substantially air tight holding tank;
- agitating the slurry in said holding tank, by bubbling methane through it, until anaerobic bacterial action commences, as indicated by a rise in temperature of the slurry to about 30° C.;
- removing the slurry from the holding tank;
- heating the slurry to about 55°-60° C.;
- transferring the slurry to at least one substantially air tight reaction tanks;
- fermenting the slurry under anaerobic conditions in said reaction tank at a temperature of about 55°-60° C. and agitating it by bubbling methane gas through it to promote the production of methane gas;
- collecting the gas produced in said reaction tank;
- transferring the slurry from said reaction tank to a sludge tank in which the liquid and solid phases separate; and
- recycling the liquid phase from said sludge tank to the mixing step and to the holding tank.

8. Process according to claim 7, wherein the slurry has a solids content of 5–10%.

9. A process according to claim 7, further comprising:
- separating the collected gas into by-products and methane; and
- recycling part of said methane to the holding tank and the reaction tank to agitate the slurry.

10. A process according to claim 7, further comprising:
- heating the contents of the sludge tank under anaerobic conditions to produce a further yield of methane.

11. A process according to claim 7, further comprising:
- heating the contents of the sludge tank to a temperature sufficient to sterilize the sludge.

* * * * *